(12) United States Patent
Roy et al.

(10) Patent No.: US 9,952,041 B2
(45) Date of Patent: Apr. 24, 2018

(54) ASSESSING ALIGNMENT OF TOP AND BOTTOM ENDS OF TSVS AND CHARACTERIZING MICROFABRICATION PROCESS

(71) Applicant: Rudolph Technologies, Inc., Flanders, NJ (US)

(72) Inventors: Rajiv Roy, Dallas, TX (US); David Grant, Thousand Oaks, CA (US); David S. Marx, Newbury Park, CA (US); Hanh Chu, Edina, MN (US)

(73) Assignee: Rudolph Technologies, Inc., Wilmington, MA (US)

( * ) Notice: Subject to any disclaimer, the term of this patent is extended or adjusted under 35 U.S.C. 154(b) by 190 days.

(21) Appl. No.: 14/762,613

(22) PCT Filed: Jan. 23, 2014

(86) PCT No.: PCT/US2014/012827
§ 371 (c)(1),
(2) Date: Jul. 22, 2015

(87) PCT Pub. No.: WO2014/116878
PCT Pub. Date: Jul. 31, 2014

(65) Prior Publication Data
US 2015/0362314 A1 Dec. 17, 2015

Related U.S. Application Data (60) Provisional application No. 61/755,923, filed on Jan. 23, 2013.

(51) Int. Cl.
*G01B 11/02* (2006.01)
*G01B 11/27* (2006.01)
*G01B 9/02* (2006.01)
(Continued)

(52) U.S. Cl.
CPC .......... *G01B 11/272* (2013.01); *G01B 9/0209* (2013.01); *G01B 9/02044* (2013.01);
(Continued)

(58) Field of Classification Search
CPC .............. G01B 11/272; G01B 9/02044; G01B 9/0209; G01N 21/95692; H01L 22/12; H01L 2224/16; H01L 2924/15311
See application file for complete search history.

(56) References Cited

U.S. PATENT DOCUMENTS

| | | |
|---|---|---|
| 6,980,015 B2 | 12/2005 | Haller et al. |
| 7,968,354 B1 | 6/2011 | Haller et al. |

(Continued)

FOREIGN PATENT DOCUMENTS

| | | |
|---|---|---|
| CN | 101709952 A | 5/2010 |
| CN | 102082108 A | 6/2011 |

(Continued)

OTHER PUBLICATIONS

PCT Search Report and Written Opinion, PCT/US2014/012827, dated Jul. 8, 2014, 13 pages.

*Primary Examiner* — Hwa Lee
(74) *Attorney, Agent, or Firm* — Dicke, Billig & Czaja, PLLC (57) ABSTRACT

A method for characterizing a microfabrication process and the product thereof is described. A substrate having TSV's formed therein is assessed by determining the geometries and positions of the top and bottom ends of a TSV. Individual TSV's as well as the entire pattern of TSV's formed in a substrate may be assessed.

9 Claims, 4 Drawing Sheets

(51) Int. Cl.
*H01L 21/66* (2006.01)
*G01N 21/956* (2006.01)

(52) U.S. Cl.
CPC ....... *G01N 21/95692* (2013.01); *H01L 22/12*
(2013.01); *H01L 2224/16* (2013.01); *H01L 2924/15311* (2013.01)

(56) References Cited

U.S. PATENT DOCUMENTS

| | | | |
|---|---|---|---|
| 8,537,213 B2* | 9/2013 | Shyu | G01N 21/956 348/79 |
| 2007/0148792 A1 | 6/2007 | Marx et al. | |
| 2008/0151253 A1 | 6/2008 | Korner et al. | |
| 2010/0321971 A1 | 12/2010 | Marx et al. | |
| 2012/0056315 A1 | 3/2012 | Chang et al. | |
| 2012/0122252 A1 | 5/2012 | Fujimori | |
| 2012/0257207 A1 | 10/2012 | Marx et al. | |
| 2012/0309118 A1 | 12/2012 | Wang et al. | |
| 2013/0015871 A1 | 1/2013 | Cleary et al. | |
| 2013/0148877 A1 | 6/2013 | Claypool | |
| 2015/0168128 A1* | 6/2015 | Xiao | G01B 11/0608 356/496 |
| 2016/0161730 A1* | 6/2016 | Nakamura | G01B 11/303 356/498 |

FOREIGN PATENT DOCUMENTS

| | | |
|---|---|---|
| DE | 10321895 A1 | 12/2004 |
| GB | 2355310 A | 4/2001 |
| JP | 2013-024734 A | 2/2013 |
| WO | 2013002179 | 1/2013 |

* cited by examiner

ASSESSING ALIGNMENT OF TOP AND BOTTOM ENDS OF TSVS AND CHARACTERIZING MICROFABRICATION PROCESS

CROSS REFERENCE TO RELATED APPLICATION

This Utility Patent Application claims the benefit of the filing date of Provisional Application No. 61/755,923, filed Jan. 23, 2013, and International Application No. PCT/US2014/012827, filed Jan. 23, 2014, both of which are herein incorporated by reference.

TECHNICAL FIELD

The present invention relates generally to the inspection of structures formed in and/or through semiconductor substrates.

BACKGROUND

The use of vias as a means for efficiently packaging semiconductor devices has grown dramatically in recent years. Unfortunately, accurate characterization of vias has led to difficulties in realizing yields often associated with more mature semiconductor fabrication processes. Accordingly there is a need to more accurately characterize the nature of vias formed in and through semiconductor substrates as part of the fabrication process of semiconductor devices and packages.

DETAILED DESCRIPTION

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims and equivalents thereof.

Figure 1:
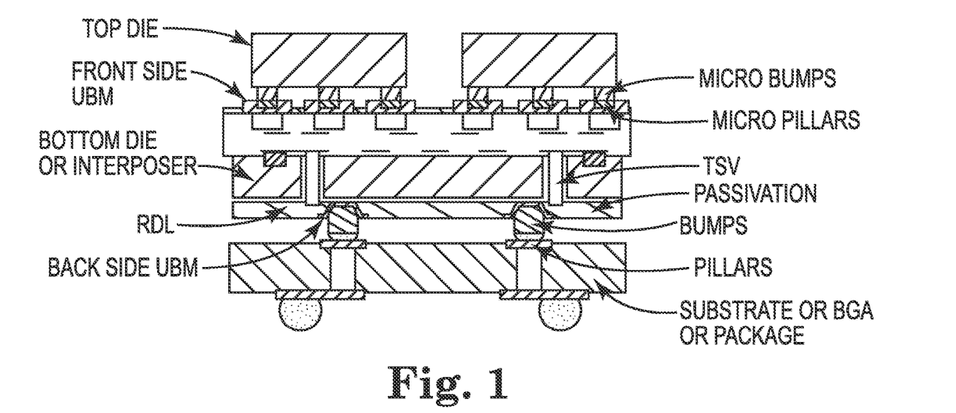
FIG. 1 is a schematic cross section of a prior art, and ideal semiconductor device formed using 3D packaging techniques.

In FIG. 1 can be seen a cross section of an ideal semiconductor device packaged using advanced 3D packaging techniques. Rather than using actual wires (gold or copper), individual chips or die are connected to external electronic infrastructure such as, for example, circuit boards, by means of an interposer and a ball grid array package. As can be seen in the image, through silicon vias or TSV's are used to electrically connect the die coupled to or formed as part of the front side of the package. In general TSV's are simply a bore formed through a substrate that is filled with a conductive material to pass currents through the substrate. Accordingly, configurations and applications for TSV's other than that pictured in FIG. 1 are contemplated.

Because the purpose of a TSV is to conduct currents through a dielectric substrate, problems can arise where the TSV has an anomalous cross section, is misplaced, is omitted or is otherwise malformed. In each of these cases the TSV will fail to fulfill its current carrying function. A certain amount of variation in the location and form of a TSV is allowed, but excessive variation will lead to lower fabrication yield, unreliability and economic loss.

Figure 2A:
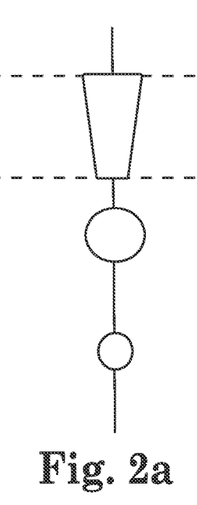
FIGS. 2a-2c are cross sectional representations of vias having varying degrees of tapering profiles.
Figure 2B:
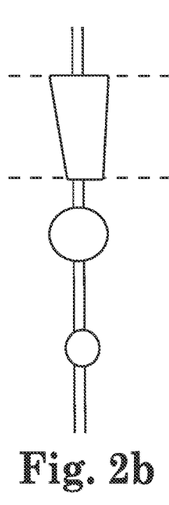
Figure 2C:
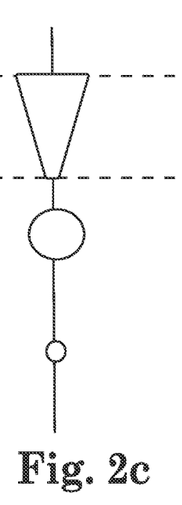

As can be seen in FIG. 1, an ideal TSV would have a regular cross-sectional shape. Generally an ideal TSV would be a uniform polyhedral or a cylinder. In this case the electrical properties would be substantially uniform along its entire depth or length. Because of the nature of the microfabrication processes normally used to create TSV's however, TSV's may tend to approximate the shape of a truncated cone, i.e. the frustum of a cone as seen in FIG. 2a. This may be acceptable under certain circumstances but must be monitored to properly manage yield. Depending on the nature of the process used to form the TSV, the TSV may also become asymmetrical as shown in the example of FIG. 2b. This type of asymmetry may, depending on its extent, result in unacceptable electrical characteristics (e.g., current carrying capacity, resistance, capacitance) or in a geometric misplacement that makes electrical connection difficult, unreliable or even impossible. Other discrepancies may result from microfabrication processes that are out of specification or from material variation. For example, the TSV of FIG. 2c, which has an overlarge top surface and an undersized bottom surface may result from improper operation of microfabrication tools or from local or universal properties of the substrate in which the TSV is formed that have not been identified or which have changed over time.

Figure 3:
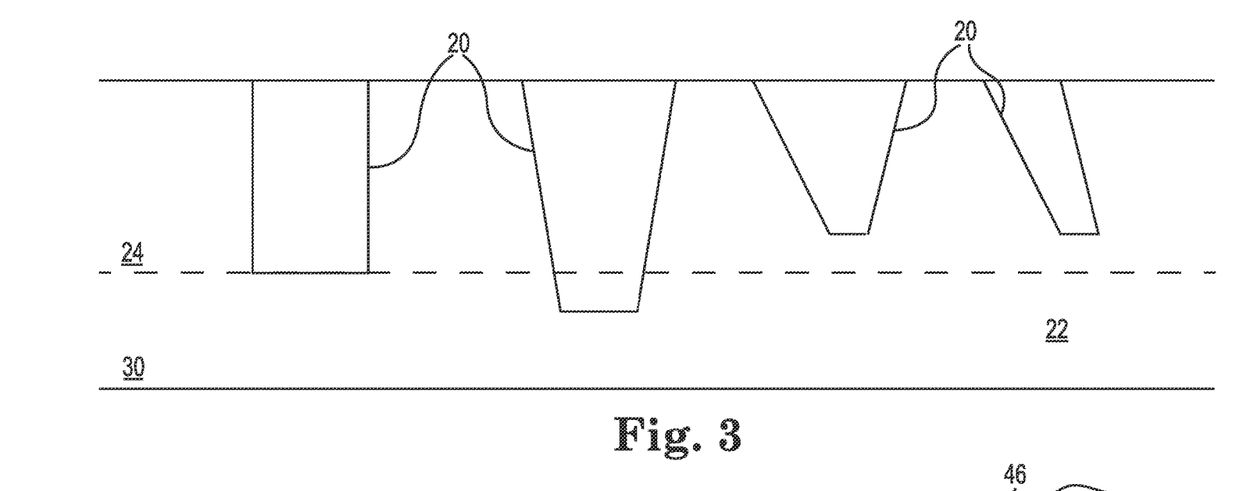
FIG. 3 is a schematic cross-section of exemplary TSV's formed in a substrate.

Assessment of TSV's and the monitoring of microfabrication processes generally takes place in a stepwise process that begins by forming a bore 20 that will eventually become a TSV into a substrate 22. As seen in FIG. 3, four separate bores 20 are formed into a substrate 22. Bores 20 are formed using known microfabrication techniques such as dry or wet etching or by ablation using lasers, focused ion beam milling or the like. Under ideal conditions, a bore 20 that is a symmetrical form such as a cylinder or a suitable polyhedron (see leftmost bore 20) will be formed. Under less than ideal conditions such as where a microfabrication tool is out of specification, bores 20 that are too large, too small, too deep, too shallow, asymmetrical, malformed or which contain debris may be formed. Note that in FIG. 3 dashed line 24 indicates a depth to which a bore 20 is to be formed. This depth is typically reached by applying a selected microfabrication tool for a specified period of time. Where a plasma etching system is used, for example, a plasma temperature or concentration that is too high or too low may result in discrepant TSV's.

Once a bore 20 has been formed, an inspection step may be performed. The inspection step is in one embodiment a high resolution optical imaging process in which images of all or a selected few of the bores 20 are captured. An example of a an optical imaging and inspection system that may be used to capture high resolution images of the upper end of a bore 20 is sold by Rudolph Technologies, Inc. of Flanders, N.J. under the name NSX®. From the images information concerning the bores 20 may be derived, including but not limited to XY position, diameters of upper ends of the bores 20, alignment of the bores with respect to the substrate in which the bores are formed, alignment to structures on the substrates, pitch of the bores 20, skew of the bore 20 pattern, keystone defects in the bore 20 pattern, diameter variation, presence or absence and the like. The XY position and whatever other information is desired, such as the diameter of the bore 20, are recorded for later assessment. Inspection of the bores 20 may take place as the images are obtained, once all images of all selected bores 20 are captured, or the inspection may be conducted off line at a time and/or place remote from the substrate and the process and inspection systems that act upon the substrate.

Inspection may involve a simple comparison of data captured from the inspection images to a pre-determined criteria defined by the user. Alternatively the bores 20 may be assessed to determine whether and to what degree the process used to form them has changed over time and that so long as some fundamental criteria regarding size and placement are met, the otherwise different bore or substrate on which the bore(s) is formed is found to be acceptable. Note that where a single bore or set of bores is found to be discrepant it is possible that the entire substrate may be discarded as a result. Alternatively, it is more often the case that a substrate such as a silicon wafer into which the bores are formed may be divided or may be intended to be divided into discrete interposer structures for use in a single package. In this instance it makes sense to keep track of all discrepant units and to discard those that are unusable. This is often done using a simple database or data file often referred to as a wafer map. In the past discrepant portions of a substrate were marked with an ink dot to signal that the unit was unusable. In short, inspection of TSV's and their component parts at various stages in their manufacture involves a comparison of the information derived from the structures to some criteria that may be arbitrary or derived from the structures themselves. Whether a unit is to be used is entirely up to an operator of a fabrication facility and it should be noted that the necessary level of quality that a TSV and or the substrate on which it is formed may vary from operator to operator and from structure to structure.

The inspection step of capturing images of the top end of the bores 20 may take place immediately after the bores 20 are formed, after the bores 20 have been filled with a conductive material and planarized to reveal the upper end of the bore 20 or may take place at both steps. Note that in some applications the process of filling a bore 20 with a conductive material, commonly known as metallization, may obscure the upper end of the bore 20. In these instances it is desirable to perform inspection before metallization or use an inspection system that may sense a diameter of an upper end of a bore 20 through an opaque material. One such type of system is an opto-acoustic metrology system sold by Rudolph Technologies, Inc. of Flanders, N.J. under the name METAPULSE®. While it may be economical in terms of inspection equipment and/or time necessary to perform inspections after two separate microfabrication processes, it may be beneficial to capture inspection data concerning the TSV after each processing step. In some instances it is possible that information concerning TSV's may be obtained as a by-product of inspection or metrology processes such as optical inspection of circuitry or opto-acoustic metrology of structures in the surface of a substrate.

Another step in the process of assessing TSV's is the step of establishing a position of the bore 20 that forms a TSV with respect to the substrate in which it is formed. By calibrating mechanical movement means (stage/top plate) on which a substrate is supported to an imaging system that captures images of the substrate on the movement means, one is able to determine a position of the TSV/bores that are imaged by the imaging system. Similar calibration steps that determined the location of the perimeter and alignment structures of the substrate help one to establish a position the imaged TSV's with respect to the substrate itself.

TSV's may also be localized on a substrate using fiducial marks formed on the substrate which are imaged together with the TSV's. In another embodiment, features of the substrate, including circuitry or even defects such as chips, cracks or scratches, that are visible in the surface of the substrate may be used to localize the TSV's on the substrate itself or with respect to other features on the substrate. Note that as will be described below, it will be important to ensure that the coordinate system established for the localization of TSV's on the top surface of a substrate is aligned with the coordinate system that is established to localize the bottom end of TSV's on the bottom surface of a substrate.

Once the upper end of a TSV has been localized and its desired characteristics determined, it is necessary to determine the position and characteristics of the bottom end of the TSV. As indicated above, a TSV is not typically formed entirely through a substrate in one step. Rather, the bore 20 is formed partially through a substrate to a desired depth. Accordingly, it is difficult or impossible to directly view the bottom end of a TSV without using specific imaging or sensing techniques (e.g. IR imaging, IR reflectometry, IR interferometry, IR scatterometry, IR laser triangulation, or an opto-acoustic system that may be used to measure features within an opaque substrate) or without first thinning the backside of the substrate to expose a bottom end of a TSV. Note that where a substrate is made of silicon, near IR light may be used for imaging purposes as silicon is at least partially transparent to light having wavelengths in or near the near-IR range. Non-silicon substrates may be at least partially transparent to light in other wavelength ranges or TSV's may be assessed using methods that can work through opaque substrates such as the opto-acoustic metrology system described above.

Where a substrate is transparent to those wavelengths of light to which a selected inspection system is sensitive, it may be possible to reverse the substrate to direct inspection radiation (e.g. IR radiation) through the back side of a substrate to localize the bottom end of a TSV. In one technique used by Tamar Technology of Newbury Park, Calif., IR light is directed onto and through the back side of a substrate and is incident upon the bottom end of a TSV and also on the backside (interior to the substrate) of the top surface of the substrate. The signal derived from the IR light returned from the bottom side of the TSV is compared to the signal derived from the light returned from the top surface of the substrate to determine the height, or depth, of the TSV. Where an optical sensor or inspection system having sufficient resolution is used, e.g. a sensor or system having a small spot size, in addition to the depth/height of the TSV, one may obtain an accurate XY position of the TSV. In those situations where it is impractical or difficult to capture an actual image of the bottom end of a TSV, the opto-acoustic technique or a non-imaging technique such as reflectometry or scatterometry may be used. While these techniques may provide information concerning the depth/height of a TSV and in some instances an XY position of the TSV, it is difficult to obtain specific geometric data concerning individual TSV's in a rapid manner; opto-acoustic systems can be somewhat slow which may limit their use to a sampling routine and reflectometry and scatterometry tend to provide information about a group of TSV's instead of a single one. Using one of these techniques the assessment of the bottom end of a TSV may be carried out by peering through the reverse side of a substrate.

Assessment of the bottom end of a TSV may alternatively or in addition be carried out once the bottom end of a TSV has been exposed by means of thinning a wafer in a grinding process such as chemical mechanical planarization (CMP). In this type of process a wafer having TSV's formed therein has its obverse side adhered to a carrier substrate of some sort. In most cases the substrate to be thinned is glued to a sacrificial substrate that does not have TSV's or other structures formed thereon. The reverse of the substrate with the TSV's is then ground away using abrasive pads, slurries and/or chemical etchants. The grinding process things a wafer from its initial position shown by line 30 in FIG. 3 to its final position shown by dashed line 24. Ideally the bottom surface of a TSV will be located at the plane identified by line 24 (see leftmost TSV bore 20) and little, if any, material filling the bore 20 will be removed as a result of the grinding. Note however that because the process of forming TSV bores 20 can be variable, it is common practice to grind to a plane/line 24 that is closer to the obverse side of the substrate than are the nominal positions of the bottom ends of the TSV's. In this way the bottom ends of the TSV's should be uniformly exposed. Where a TSV or group of TSV's are not exposed the causes may be diverse, but for example the grinding process may inadvertently grind more heavily in one area of the substrate, thereby not exposing the TSV's in another region of the substrate or the TSV('s) may have been malformed from the beginning. In any case, once the bottom ends of the TSV's are exposed by grinding an optical inspection system is used to capture images of the TSV's. As described above with respect to the top end of the TSV's, the XY position of each TSV is noted as is its geometric characteristics (diameter, shape, etc.). The array of TSV's as seen from the reverse side of the substrate may be assessed to ensure the proper placement or presence of each TSV as well as the proper pitch and alignment (skewing, etc.). The alignment step is of key importance here as it is necessary to not only localize the individual TSV's, but to also establish the position of the bottom end of the TSV with respect to the top end of the TSV to a high degree of accuracy. Presupposing that the top and bottom ends of the TSV's are each well aligned and localized with respect to their respective sides of the substrate, using the edges of the substrate as well as alignment structures formed therein (e.g. flats or notches), to ensure that respective coordinate systems of the top and bottom of the substrate are properly aligned. Alternatively, one may utilize an IR imaging system to view a structure located (e.g. fiducials, circuitry, etc.) on the obverse side of the substrate through the riverside side of the substrate simultaneously, thereby providing a direct correlation between the coordinate systems. In another embodiment one may utilize a system arranged to simultaneously view selected features on both the obverse and reverse sides of the substrate. If properly calibrated, such a system, which often use mirrors and/or fiber optic structures, can directly compare the position of features of the obverse and reverse sides of the substrate. In some instances software may be used to obtain a best or most likely fit between the locations of the top and bottom ends of the TSV's themselves. Such an alignment may be double checked by using the same images and/or the same software to match the position of the edges and any alignment structures of the substrate, e.g. three point edge finding in addition to angular alignment by matching of notches or flats.

In FIG. 3 an assessment of the TSV's pictured would reveal that the left two TSV's are present and accounted for. The top and bottom ends can be checked to determine whether they are in the correct locations. The diameter and shape of the top and bottom ends of the TSV's may be compared to determine whether the microfabrication technique used to form the TSV's as well controlled. The leftmost TSV is in this example a representative of an ideal TSV. The second from the left TSV has the truncated cone shape described above and a much larger top end than a bottom end. The disparity between the sizes of the top and bottom ends may or may not pass muster depending on the criteria established by the operator of the fabrication facility. Further, the second from the left TSV appears to be symmetrical about a vertical axis (supposing that the nominal shape is cylindrical or conical and not polyhedral). Note that while images of the top and the bottom of the TSV may not include much, if any, information about the shape or profile of the TSV between the obverse and reverse sides of the substrate, the profile or shape of the TSV may be inferred to some degree. Because the thickness of the substrate is or can be known from the grinding process, this information, along with the XY position of the ends of the TSV and the shape of the ends of the TSV can be used to infer the shape of the interior portions of the TSV. Inferences drawn from geometric information taken together with information about how specific microfabrication techniques function may allow for more complex models of TSV interior structures as necessary.

In FIG. 3 the two right TSV's are too short and their bottom ends are not exposed at line/plane 24 after grinding. Note that the problem of TSV's that are too deep may be correlated with larger top end diameters or with bulbous sidewalls instead of straight where the microfabrication technique that is in use (e.g. dry or wet etching) is applied for too long a time or at settings that are too strong for the given substrate. Note that a too long TSV is not necessarily problematic, i.e. it may yet function, but will represent a loss in terms of time or materials lost in extra processing or grinding. In some cases grinding may be somewhat uneven if a group of too long TSV's is sufficiently harder or tougher than the substrate in which they are formed. In this case the substrate may be ground so as to have obverse and reverse sides that are not parallel to one another.

Importantly, one can see that the right two TSV's in FIG. 3 are not symmetrical about an axis normal to the obverse and reverse sides of the substrate. This can be due to misalignment of microfabrication tools or by the movement means being itself misaligned or perhaps where a debris of some type is interposed between the substrate and the movement means. Again, this type of misalignment may not rule out the use of a substrate so long as the TSV's retain sufficient placement accuracy to make the required electrical connections in a semiconductor device package.

Figure 4:
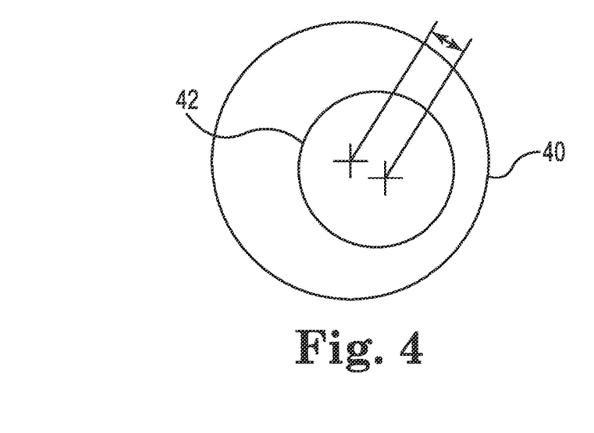
FIG. 4 is a schematic illustrate showing a determination of an offset in size and position between the ends of a TSV.

FIG. 4 illustrates a basic assessment of the magnitude of an offset between the position and geometry of the top and bottom of a TSV. Top 40 of the TSV is larger than the bottom 42. Also the bottom 42 of the TSV is smaller than the top 40. That the two ends 40, 42 are laterally offset suggests that a microfabrication tool may be misaligned or that there is debris between the substrate and the movement means on which it is supported. Depending on the desired geometry of the TSV and on the nature of the microfabrication tooling or process used, that the sizes of the top 40 and bottom 42 differ may also be indicative of the nature operation of a microfabrication tool or process. While the TSV pictured in FIG. 4 has top and bottom ends with a circular shape which together with the size difference therebetween infer a more or less frustoconical shape, it is to be understood that the TSV take on other cross section shapes such as pyramidal in which case the shapes of the top and bottom ends of the TSV may be square or rectangular.

Figure 5:
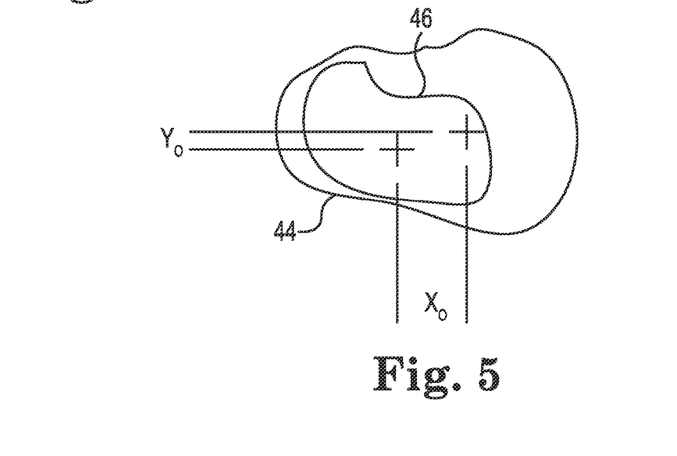
FIG. 5 is a schematic illustrate showing a determination of an offset in size and position between the ends of a TSV wherein the ends of the TSV are irregular in shape.

As can be seen in FIG. 5, it is possible for a TSV to have a somewhat irregular shape. Ideally however, the shape of the TSV will be regular and the degree to which the shape of the top and bottom ends of the TSV depart from the pre-defined or desired regular shape may define how well a microfabrication tool or process is functioning. Note that because the top 44 and bottom 46 ends of the TSV are irregular in shape, one may use software means such as blob analysis software to determine a centroid of the top or bottom area as suggested by the figure. The centroids may then be used to determine lateral offsets Xo and Yo as shown.

As described above, interferometers may be used to characterize TSV's and other structures including a substrate S such as a wafer. Examples of interferometers suitable for this purpose are illustrated in FIGS. 6 and 7.

Figure 6:
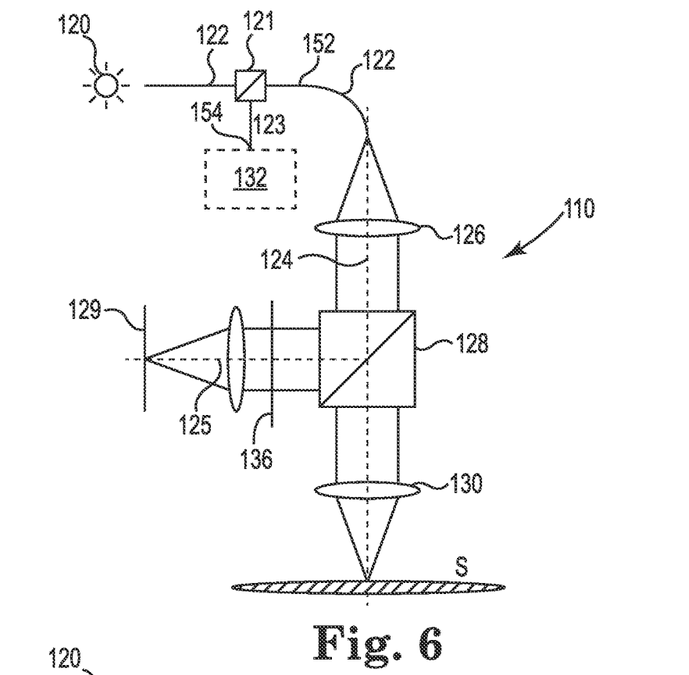
FIG. 6 is a schematic of an interferometer in which a light source and a spectrometer at least partially share a fiber optic conduit.

FIG. 6 illustrates one embodiment of an interferometer 110 that may benefit from the application of principles disclosed herein. FIG. 7 illustrates another, similar interferometer 110' that may also benefit from the application of principles disclosed herein.

Figure 7:
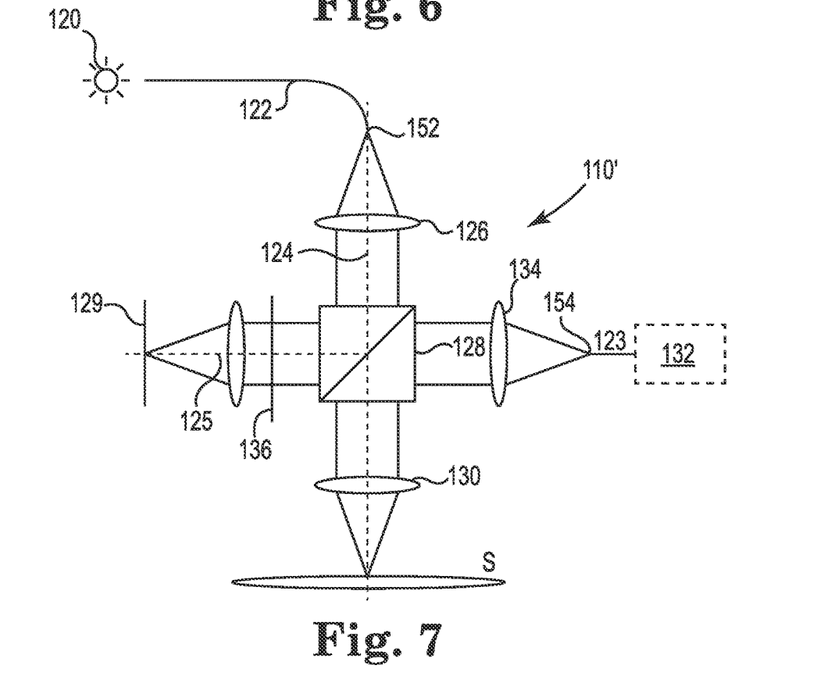
FIG. 7 is a schematic of an interferometer in which a light source and a spectrometer are positioned on separate legs of the optical system.

In FIGS. 6 and 7 multi-spectral or broadband illumination is emitted from a light source 120. The light source may be a simple broadband source such as a halogen, xenon, fluorescent or incandescent or similar. Essentially any light source that emits whatever wavelengths of light needed for a specific application will suffice. The interferometers 110 and 110' collect and conduct light emitted from the light sources 120 by means of fiber optic cables 122. Note that light emitted from sources 120 may propagate through open air in lieu of cables 122.

In both interferometers 110 and 110' light from source 120 is emitted along optical path 124. In the case of interferometer 110 in FIG. 6, light passes through a beam splitter 121 before being emitted onto the optical path 124. Optical element 126, which may include one or more lenses, filters or stops, collimates the light traveling along optical path 124. This collimated light passes through beam splitter 128 and is in turn focused by objective 130 onto a substrate S. Note that the objective 128 may include one or more lenses, filters or stops, as will be understood by those skilled in the art.

Light incident upon the substrate S is at least partially returned along optical path 124 and is re-collimated by the objective 130. Collimated light from objective 130 is in the embodiment of FIG. 6 returned along optical path 124 to optical fiber 122, which conducts the returned light to beam splitter 121. At least a portion of the light returned from the substrate S to beam splitter 121 is directed to a spectrometer 132 by optical fiber 123.

In the case of interferometer 110' of FIG. 7, light returned from the substrate S through objective 130 is at least partially directed by beam splitter 128 through lens 134 to spectrometer 132. Note that lens 134 may be any useful combination of optical elements such as individual lenses, filters and stops.

In both interferometers 110 and 110', beam splitter 128 directs a portion of the light emitted by light source 120 along optical path 125. Optical path 125 defines what is often referred to as the reference leg of an interferometer. Optical path 124 is often referred to as the sample leg of an interferometer. Light directed along optical path 125 is, in the end, simply returned to the beam splitter 128 without significant modification. Light returned along the optical paths 124 and 125 interfere with one another to produce interference fringes. These interference fringes are sensed as a function of the wavelength of light by the spectrometer 132.

The interferometer 110 illustrated in FIG. 6 has the advantage of permitting both the light source 120 and the spectrometer 132 to be located remote from the remainder of the interferometer 110. This can aid in the optomechanical packaging of a profilometer based on the interferometer 110. Unfortunately, the addition of beam splitter 121 in the fiber optic 122 reduces the intensity of light that ultimately reaches the spectrometer. For particularly "dark" substrates S, i.e. for substrates that are not particularly reflective, the signal output by the spectrometer can be relatively low due to the lack of light. This may result in a poor measurement where the signal to noise ratio is particularly low.

The interferometer 110' illustrated in FIG. 7 overcomes poor signal to noise ratios by omitting the beam splitter 121 and locating the sensor leg of the interferometer 110' adjacent to the beam splitter 128. This modification results in a slightly larger optomechanical package, however the spectroscope 132 may yet be located remotely where a fiber optic cable 123 is used.

Balancing of Intensities[1]

[1] http://www.rp-photonics.com/spotlight_2009_05_22.html

It has been noted in the literature that signals having dissimilar magnitudes may yet interfere with one another to product an interference signal or fringe. However in certain circumstances, as will be described in more detail hereinbelow, it can be desirable to maximize interference in a system such as that shown in FIGS. 6 and 7.

In the reference leg of an interferometer such as interferometers 110 and 110', a reflector of some sort is used to return light diverted along optical path 125 to the beam splitter 128. In FIGS. 6 and 7 this reflector is represented by a generic mirror 129, though other options are available as will again be described in more detail hereinbelow. Generally speaking, a mirror 129 has a high reflectance and will return a large percentage of the light incident upon it along optical path 125. The same cannot always be said for the substrate S. Where there is a reflectance mismatch between the surface of the substrate S and the mirror 129, the resulting interference signal may not be optimal. Accordingly, it may be advantageous to match, at least to a degree, the magnitude of the signals that are joined by the beam splitter 128.

Matching the magnitude of the signals joined by the beam splitter 128 may be effected by attenuating the light on one of the optical paths 124, 125 or by modifying how the beam splitter 128 divides light from the light source 120 along paths 124, 125. Where the signal to noise ratio is sufficiently high, one may attenuate light on one of the optical paths 124, 125 such that the amount of light from each path that contributes to the interfered light signal provided to the spectroscope 132 is within a predetermined range of proportions. In one exemplary embodiment, the amount of light reaching the spectrometer from each optical path 124, 125 is approximately the same. Note that by attenuating light along one of the optical paths 124, 125 the magnitude of light reaching the spectrometer 132 will be lower and it is more likely that a less useful signal may be derived therefrom.

In one embodiment light traveling along optical path 125 is attenuated by placing a neutral density filter 136 along the optical path 125. In a preferred embodiment, the neutral density filter 136 is part of a modifiable filter apparatus (not shown) of a useful type. For example, the neutral density filter 136 may simple be one of a number of different filters in a filter wheel. By modifying the position of the filter wheel one may select a suitable neutral density filter 136. In another example, the neutral density filter 136 may be mounted in a holder that permits manual replacement of the filter to select an appropriate attenuation of light along the optical path 125. In yet another example, one may use a modifiable spatial light modulator as a neutral density filter 136. A spatial light modulator is an LCD device that can modify the amplitude, phase, or polarization of light waves in space and time. Note that the neutral density filter 136 may be positioned in one or both of optical paths 124 and 125.

In another embodiment, a fixed neutral density filter 136 may be used in one or both of the optical paths 124 and 125. Generally speaking, where the interferometer 110 or 110' is to be used in a setting in which there is a high rate of turnover in the substrates S such that optimization or balancing of the magnitudes of the light returned from the respective optical paths 124, 125 must change frequently, it is more likely that a modifiable filter 136 would be suitable. Conversely, where the nature of the substrates S is fairly consistent, then a fixed filter 136 may be suitable. One will appreciate that the increased complexity of modifiable filters 136 will increase the cost and complexity of the interferometer in which they are used. Fixed filters 136 are less flexible but are also much more inexpensive.

Where it is desirable to not attenuate light propagating along optical paths 124 or 125 it may be desirable to select an appropriate beam splitter 128. In one embodiment a suitable fixed beam splitter 128 is provided at the intersection of optical paths 124 and 125 to optimize the magnitude of the light propagating along these paths. For example, where the reflectance of the substrate S is lower than that of the mirror 129, a beam splitter 128 may be selected to accommodate for the difference in reflectance by directing more light along optical path 124 than along optical path 125.

As above, where the nature of the substrates S changes frequently, the beam splitter 128 may be changed frequently on a manual basis. In one embodiment cube, pellicle or other suitable types of beam splitters are manually switched to optimize the magnitudes of light propagating along optical paths 124, 125. In another embodiment, an electrically modifiable beam splitter may be used, though it will be understood by those skilled in the art that beam splitters whose characteristics can be electrically controlled are still under development and may not be feasible in the near future. In any case, by carefully employing filters 136 and/or beam splitters 128 having suitable characteristics, it is possible to optimize the magnitudes of the light propagating along optical paths 124 and 125 to thereby optimize the resulting signals output by a spectrometer 132.

In the design of optical systems such as a microscope, it is desirable to minimize chromatic aberration. This typically improves the results one is after. In interferometers this often takes the form of matching the optical elements of the sample and reference legs of the device. In so doing one ensures that the aberration from both legs is essentially the same and as a result noise in the final signal is believed to be minimized. While this may be true, it has been found that matching the aberration of optical elements in the reference and sample legs of an interferometer can result in significant "null" zones in the measurements obtained from the device. Accordingly, it is one aim of this invention to minimize the extent of the aforementioned null zones by introducing into the respective legs of an interferometer a differential chromatism, i.e. a quantized chromatic aberration in each leg that differs between the legs. It is to be understood that a "different" chromatic aberration may be introduced into either leg of an interferometric optical system and that the examples below are not limiting in this way.

Figure 8A:
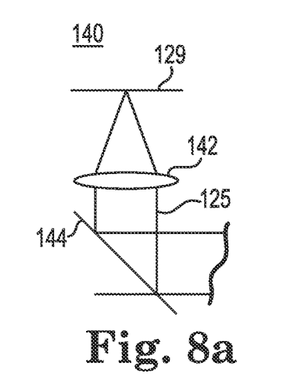
FIGS. 8a-8c are schematic views of optical components which can be used to impose differential chromatism within an optical system.
Figure 8B:
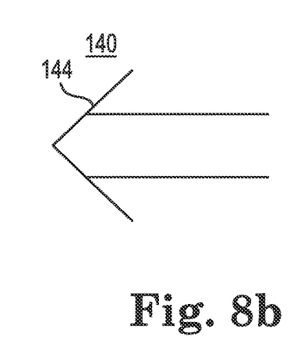
Figure 8C:
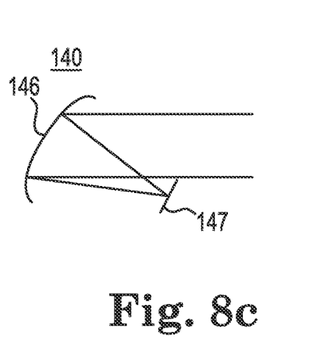

FIGS. 8a-8c illustrate schematically three ways in which differential chromatism may be imposed upon an interferometric optical system. Note that the reference leg variations illustrated in FIGS. 8a-8c and variations thereof may form part of optical path 125 of an interferometer 110 or 110' (FIGS. 6 and 7). FIG. 8a illustrates a first embodiment of a reference leg 140 of an interferometer. Reference leg 140 receives light from a beam splitter (not shown) such as beam splitter 128. This light is directed along optical path 125 to a reflector 129. In this embodiment light is focused onto the reflector 129 by an optical element 142. Light reflected by reflector 129 is collimated and returned along optical path 125 towards the beam splitter (not shown) that directed light along optical path 125 in the first instance. At least a portion of the light returned along optical path 125 passes through the beam splitter (not shown) and then on to the spectrometer 130. The optical path 125 in the embodiment of FIG. 8a includes an optional turning mirror 144 that is useful for optomechanically fitting the interferometer 110, 110' into a given space.

The optical element 142 shown in FIG. 8a may have substantially the same chromatic aberration as an objective placed in the sample leg of an interferometer, in which case the effects of chromatic aberration on interferometric measurements is reduced but the problem of null zones is increased. Alternatively, the optical element 142, which may consist of one or more individual lenses, filters or stops, may have a different amount of chromatic aberration than the objective of the reference leg, i.e. may induce differential chromatic aberration. In this latter case chromatic aberration may be increased, but null zones are minimized. Generally speaking a reflector 129 will not induce much in the way of chromatic aberration. That being said, it is preferable to take into consideration the possibility that coatings or the like on the reflector 129, alone or in combination with the optical element 142, may define a different chromatic aberration than either of the reflector or optical element taken alone.

FIG. 8b illustrates a reference leg 140 that utilizes a reflector cube or retroreflector 144 to return light along the optical path 125 without introducing much, if any chromatic aberration to the returned light. In this instance differential chromatism is induced by using an objective having a known chromatic aberration in the sample leg of an interferometer. Since the retroreflector 144 induces little, if any chromatic aberration, the resulting interferometer is said to exhibit differential chromatism between its reference and sample legs.

FIG. 8c illustrates a reference leg 140 that incorporates the use of a mirror 146 having a predetermined optical power to return light along optical path 125. Mirror 146 reflects and focuses light onto mirror 147 which returns the light to mirror 146 which in turn collimates and returns the light to the beam splitter. Note that the exact optical power is highly dependent upon the optical system in which it is utilized and accordingly, no explicit example is provided here. The exact power and placement of a mirror 146 having optical power may easily be determined by one skilled in the art of optical design using classical or numerical automated optical design techniques.

Figure 9:
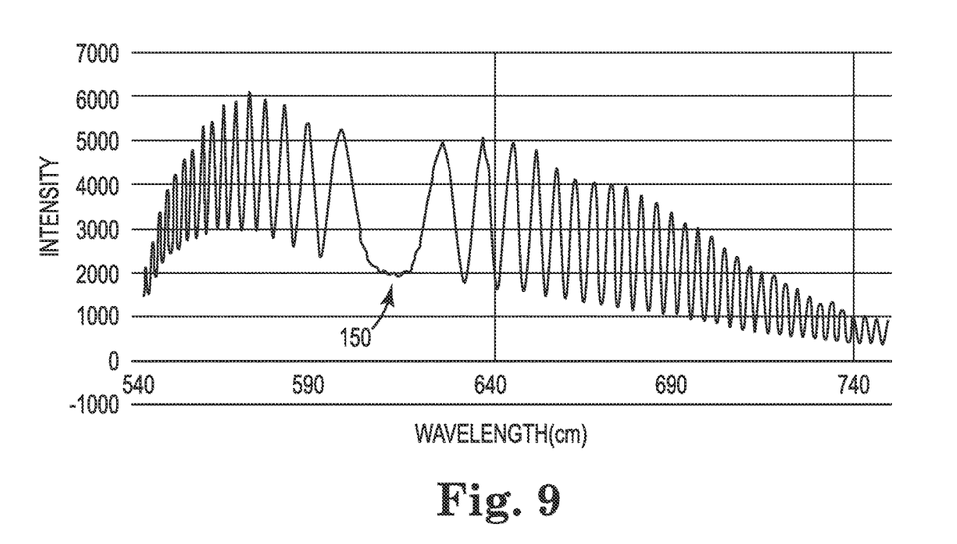
FIG. 9 is a schematic representation of an interferogram, which relates the intensity of interference fringes sensed by an interferometer to the wavelength of interfering light.

FIG. 9 is a schematic representation of an interferogram, which relates the intensity of interference fringes sensed by the interferometer 110, 110' to the wavelength of the interfering light. Note that this interferogram is obtained at given position of the interferometer relative to the substrate S. As will be appreciated, the position of the interferometer is fixed relative to the substrate and it is the position of features of the substrate S that vary with respect to their position along the optical path 124.

In one embodiment of the present invention, the spectrum of light used by the interferometer 110, 110' includes infrared wavelengths and accordingly, in addition to being capable of localizing an upper surface of a substrate S made of silicon, the interferometer is capable of localizing features within the silicon substrate S. One such structure may be, for example, a bottom surface of a TSV as described hereinabove.

As can be seen in FIG. 9, there exists a null value or space 150 in the intensity data at approximately 612 nm. This null value 150 is a result of a lack of interference at the specified wavelength range. This position and extent of this null value 150 depends upon the nature of the optical system that forms the interferometer 110 or 110' and the nature of the substrate S. Where this null value 150 is wide, it can be difficult to obtain information that is necessary to properly localize and characterize the substrate S that is under test. Where the reference leg and sample legs of the interferometers 110 and 110' have substantially the same chromatic aberration, i.e. where the differential chromatism of the respective legs is minimized, the null value 150 extends over a relatively larger area. Such an interferometer 110 or 110' subsequently has a gap in its output that makes it more difficult to fully characterize a substrate S. Introducing a specified amount of differential chromatism minimizes or in some instances, practically eliminates the null value 150 and improves the performance of the interferometer 110 or 110'.

Another problem that may be caused by the null value 150 is where this gap in the useful data obtained from the spectrometer 132 corresponds to positions, structures or characteristics that are of interest on the substrate S. It has been found that by modifying the input and output apertures 152, 154 of the interferometers 110, 110', one may be able to move the null value 150 to a position that is outside of the desired range of sensitivity or to at least move it to a location where the negative effects of the null value 150 are minimized. Making the apertures 152, 154 larger or smaller may move the position of the null value 150 to the left or the right on the graph shown in FIG. 9. Where the structures of interest on the substrate S are typically identified or characterized at the wavelengths to the right or left of the null value 150, a more reliable and certain measurement may be obtained.

In the case of the interferometer 110 illustrated in FIG. 6, the input aperture 152 is also the output aperture 154 of the interferometer 110. This is a result of the fact that the fiber optic conducts light in two directions. In this embodiment, the input and output apertures 152, 154 may be defined by the diameter of the fiber optic 123 itself or by a physical aperture (not shown) which may be of a fixed diameter or of a modifiable diameter, i.e. a changeable iris may be used. Note that it is important to ensure that the input and output apertures be conjugate with one another.

In the interferometer 110' illustrated in FIG. 7, the input and output apertures 152, 154 are located in separate legs of the optical system. As with interferometer 110, the input aperture 152 is located at the end of the fiber optic 123. Note that where fiber optics are not used and the light propagates in air, a simple aperture of fixed or modifiable diameter may be used. The output aperture 154 is located adjacent (optically) the spectrometer, and again may simply be defined by the input end of the fiber optic 123 or may be defined by a fixed or modifiable aperture. Again, the apertures are, or should be, as near as conjugate as is possible.

Although specific embodiments of the present invention have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of assessing a quality level of a through silicon via (TSV) formed in a substrate defining an obverse side opposite a reverse side, the method comprising:
   obtaining geometric information about a top end of a TSV from the obverse side of the substrate;
   obtaining geometric information about a bottom end of the TSV from the reverse side of the substrate;
   wherein the steps of obtaining geometric information about a top end and obtaining geometric information about a bottom end are performed simultaneously by an automated inspection system:
   aligning the geometric information of the top and bottom ends of the TSV to determine an alignment of the respective top and bottom ends of the TSV.

2. The method of assessing a quality level of a through silicon via (TSV) of claim 1 further comprising obtaining a thickness value of the substrate substantially at an XY position of the TSV and inferring a geometric volume of the TSV based at least on the geometric information of the respective top and bottom ends of the TSV and determining whether the inferred geometric volume of the TSV is similar to a predetermined criteria.

3. A method of characterizing a microfabrication process and a product formed by the microfabrication process comprising:
   determining a location of a plurality of TSV's from an obverse side of a substrate;
   determining a location of the same plurality of TSV's from a reverse side of the substrate, the reverse side being opposite the obverse side;
   wherein the steps of determining a location of a plurality TSV's from an observe side and a reverse side are performed simultaneously by an automated inspection system;

determining the presence of a misalignment between the position of a TSV from the obverse and reverse sides of the substrate; and, identifying, a process excursion in a microfabrication process based upon the determined presence of a misalignment.

4. The method of characterizing a microfabrication process and a product formed by the microfabrication process of claim 3 further comprising:

determining a geometry of the plurality of TSV's from both the obverse and reverse sides of the substrate; and, determining whether the geometry of the respective TSV's from the respective obverse and reverse sides of the substrate varies by more than a predetermined criteria selected from a group consisting of size and geometry.

5. The method of characterizing a microfabrication process and a product formed by the microfabrication process of claim 3 further comprising:

fitting the location of the plurality of TSV's as determined from the obverse side of the substrate to the location of the plurality of TSV's as determined from the reverse side of the substrate; and, quantifying the degree of misalignment between the fitted locations of the TSV's, if any.

6. The method of characterizing a microfabrication process and a product formed by the microfabrication process of claim 3 wherein determining a location of a plurality TSV's from an obverse side of a substrate is conducted prior to the filling of the TSV with a conductive material (metallization).

7. The method of characterizing a microfabrication process and a product formed by the microfabrication process of claim 3 wherein determining a location of the same plurality of TSV's from a reverse side of a substrate is carried out after the substrate has been thinned from a nominal thickness.

8. A method of characterizing a microfabrication process and a product formed by the microfabrication process comprising:

determining a location of a plurality of TSV's from an obverse side of a substrate;

determining a location of a bottom end of the same plurality of TSV's within the substrate;

wherein the steps of determining a location of a plurality of TSV's and a location of a bottom end of the same plurality of TSV's are performed simultaneously by an automated inspection system;

determining the presence of a misalignment between the position of a TSV from the obverse side of the substrate and the position of the bottom end of the TSV within the substrate and, identifying a process excursion in a microfabrication process based upon the determined presence of a misalignment.

9. The method of characterizing a microfabrication process and a product formed by the microfabrication process of claim 8 further comprising the use of radiation in the near infrared range of wavelengths to obtain a position of the bottom end of the TSV's.

* * * * *